(12) United States Patent
Masson et al.

(10) Patent No.: US 7,018,332 B1
(45) Date of Patent: Mar. 28, 2006

(54) CIRCUMFERENTIAL RETRACTOR APPARATUS

(75) Inventors: Marcos V. Masson, Houston, TX (US); Mark Henry, Houston, TX (US)

(73) Assignee: SI-1, Inc., Conroe, TX (US)

( * ) Notice: Subject to any disclaimer, the term of this patent is extended or adjusted under 35 U.S.C. 154(b) by 0 days.

(21) Appl. No.: 10/246,567

(22) Filed: Sep. 18, 2002

Related U.S. Application Data

(63) Continuation of application No. 09/916,819, filed on Jul. 30, 2001, now abandoned.

(51) Int. Cl.
*A61B 1/32* (2006.01)

(52) U.S. Cl. ...................... 600/227; 600/206; 600/210; 600/217; 600/201

(58) Field of Classification Search ................ 600/201, 600/206, 210, 213, 217, 219, 226, 227, 229, 600/235, 237
See application file for complete search history.

(56) References Cited

U.S. PATENT DOCUMENTS

| | | | | | |
|---|---|---|---|---|---|
| 170,573 | A | * | 11/1875 | Lesh | 267/74 |
| 569,839 | A | * | 10/1896 | Roeloffs | 600/213 |
| 744,204 | A | * | 11/1903 | Jordan | 600/242 |
| 1,389,436 | A | * | 8/1921 | Cameron | 600/219 |
| 1,450,419 | A | * | 4/1923 | Hedibrink | 600/237 |
| 2,238,563 | A | * | 4/1941 | Jacques | 27/21.1 |
| 3,762,401 | A | * | 10/1973 | Tupper | 600/217 |
| 4,200,089 | A | * | 4/1980 | Inoue | 600/242 |
| 4,559,677 | A | * | 12/1985 | Tracy | 24/300 |
| 5,030,224 | A | * | 7/1991 | Wright et al. | 606/151 |
| 5,163,419 | A | * | 11/1992 | Goldman | 600/206 |
| 5,964,697 | A | | 10/1999 | Fowler | |
| 5,964,698 | A | | 10/1999 | Fowler, Jr. | |
| 6,117,072 | A | | 9/2000 | Fowler, Jr. | |
| 6,409,731 | B1 | * | 6/2002 | Masson et al. | 606/86 |

OTHER PUBLICATIONS

"Retractor Hooks attache to elastic coupler", Surgical Products, Oct. 1999, p. 1.
"Surgical Retractor Hooks"; Orthopedic Technology Review, Jan. 2000, and Apr. 2000.
"The Lone Star Retractor System", Journal of Hand Surgery, Jan. 2000.
"The Lone Star Retractor System", Outpatient Surgery Magazine, Jan. 200, Feb., 2000, and Apr. 2000.
"Retract with Ease", Outpatient Surgery Magazine, May 2000.
"The Lone Star Retractor System", Foot & Ankle, Jan. 2000 and Feb. 2000.

* cited by examiner

*Primary Examiner*—Pedro Philogene
*Assistant Examiner*—David A Bonderer
(74) *Attorney, Agent, or Firm*—Browning Bushman P.C.

(57) ABSTRACT

A circumferential retractor apparatus including a first retractor paddle having a grasping surface and a body portion supporting the grasping surface, a second retractor paddle having a grasping surface and a body portion supporting the grasping surface and an elastic member having one end received by the first retractor paddle and an opposite end received by the second retractor paddle. Each of the paddles has a hole formed therein of a size suitable for allowing the elastic member to pass therethrough. A slot is formed in the body portion so as to open to the hole. The slot is of a tapered configuration so as to have a wide end opening to the hole and a narrow end away from the hole. The grasping surface includes a plurality of fingers extending outwardly of the body portion. Each of the plurality of fingers are arranged in parallel spaced relationship to each other. The elastic member is a length of surgical tubing.

19 Claims, 3 Drawing Sheets

CIRCUMFERENTIAL RETRACTOR APPARATUS

RELATED U.S. APPLICATIONS

The present application is a continuation application under 37 C.F.R. §1.53(b) U.S application Ser. No. 09/916,819, filed on Jul. 30, 2001, now abandoned entitled "CIRCUMFERENTIAL RETRACTOR APPARATUS" by the same inventor. The present application claims priority as a continuation application under 35 U.S.C. §120 to parent application 09/916,819.

STATEMENT REGARDING FEDERALLY SPONSORED RESEARCH OR DEVELOPMENT

Not applicable.

REFERENCE TO MICROFICHE APPENDIX

Not applicable.

FIELD OF THE INVENTION

The present invention relates to surgical retractors. More particular, the present invention relates to circumferential retractors.

BACKGROUND OF THE INVENTION

Surgical "retraction" is the drawing back of body tissue. When the operation involves making an incision, the incision itself often must be retracted. During surgery, internal organs, bones and tissues are intermittently retracted through the opening created in the retracted incision.

In certain surgeries, an assistant's fingers are used as retractor paddles. However, greater technical ease is available through the use of various mechanical retractor systems. Mechanical retractor systems can be divided into two major groups: externally mounted "fixed" to the operating table and self-retaining retractors.

The mechanical systems attached to the operating table present the same type of physical obstruction to the surgeon's movement as presented by the assistant's body, arms and hands since the externally fixed retractor systems of a vertical column, supporting arm(s) or ring and retractor paddles attached thereto. The retractor paddles, support arms or ring and vertical column in these apparatus are adjustable in multiple planes and axes of motion; however, these retractor paddles are not all independently adjustable in the vertical plane. Movement of a support arm or ring of these apparatus necessitates movement of all retractor paddles attached thereto.

Ideally, mechanical retractors, both externally mounted and self retaining, need to provide for internal organ and tissue retraction, be quickly and easily assembled, positioned and repositioned in all planes and axes of motion, present as little obstruction to the surgeon's movement as possible, protect the sterile field, diminish the risk of tissue trauma and yet be stable enough to function adequately while reducing the need for assistance.

Self-retaining retractors that have attempted to provide for internal organ and tissue retraction through the open incision have failed to permit quick, independent, easy and safe adjustment of internal organ and tissue retractor paddles in all planes and axes of motion, and in effect the prior art is either ineffectual or unsafe, or both since these paddles are not easily adjustable in the vertical plane and such internal organ and tissue retractor paddles must traverse over (or through) internal tissue before reaching the desired location along the retractor handle and/or frame. The retractor paddle depth is not highly variable and the retractor paddles' location on the retractor frame is limited.

In the past, various patents have issued relating to such retractors. For example, U.S. Pat. No. 5,520,610, issued on May 28, 1996 to Giglio, describes a self-retaining retractor. This retractor includes flexible, resilient retractor paddles which can be placed into the incision. A rigid frame is provided which includes two interlocking halves laid longitudinally over the incision. The incision retractor paddles are manually clipped to each frame half, and then the frame halves are opened to the desired extent. The incision retractor paddles and the frame provide the apparatus with stability for retraction of internal organs and tissues through the open incision by the addition of mounting jigs containing adjustment posts onto mounting means which radiate outwardly from the frame.

U.S. Pat. No. 5,931,777, issued on Aug. 3, 1999 to G. A. Sava, teaches a tissue retractor with particular use in spinal surgery. This tissue retractor includes a pair of pivotally linked arms, each with a blade mounted thereto by a ball-and-socket joint so as to allow free movement of the blades relative of the arms. The blades have an anchoring end to anchor to the bone. The retractor is operable by placing the blades in a wound opening, securing the anchoring ends to a portion of the bone in a position apart from each other, and operating the retractor to cause the blades to separate and to retract tissues surrounding the wound opening by outward pivoting of the blades relative to the position of the anchoring ends.

U.S. Pat. No. 6,074,343, issued on Jun. 13, 2000 to Nathanson et al., describes a surgical tissue retractor comprised of a plurality of retractor blades that can be operated simultaneously. Right and left retractor blades are mounted on an actuator mechanism that spreads or expands the blades as a rotatable primary actuator knob is rotated. A third retractable arm is mounted for simultaneous operation with the right and left retractor blade or independent operation through a secondary rotatable actuator knob that extends or retracts a threaded shaft attached to the center retractor blade.

U.S. Pat. No. 6,090,043, issued on Jul. 18, 2000 to Austin et al., describes a tissue retractor including a hook, a handle and an elastomeric band. The hook has a tissue-engaging portion and is retained by the handle such that the tissue engaging portion extends from a first end of the handle. The handle end of the band is retained by a second end of the handle. The back has a longitudinal body and at least one hub disposed about the body.

It is an object of the present invention to provide a circumferential retractor apparatus which properly maintains the incision in an open position.

It is another object of the present invention to provide a circumferential retractor apparatus which minimizes damage to the tissues along the edges of the incision.

It is a further object of the present invention to provide a circumferential retractor apparatus which can provide immediate feedback to the surgeon as to the amount of tension that is applied to the retracted tissues.

It is another object of the present invention to provide a circumferential retractor apparatus which is stably supported on the skin.

It is a further object of the present invention to provide a circumferential retractor apparatus which is easy to use, relatively inexpensive and easy to manufacture.

It is still a further object of the present invention to provide a circumferential retractor apparatus which is disposable.

These and other objects and advantages of the present invention will become apparent from a reading of the attached specification and appended claims.

BRIEF SUMMARY OF THE INVENTION

The present invention is a circumferential retractor apparatus comprising a first retractor paddle having a body portion supporting a grasping surface, a second retractor paddle having a body portion supporting a grasping surface and an elastic member having one end received by the first retractor paddle and an opposite end received by the second retractor paddle.

In the preferred embodiment of the present invention, each of the first and second retractor paddles is of an identical configuration. Each of the retractor paddles has a hole formed in the body portion. One end of the elastic member extends through the hole in the first retractor paddle. The opposite end of the elastic member extends through the hole in the second retractor paddle.

The body portion has an arcuate portion. A pair of blocks are connected to the bottom of this arcuate portion. The pair of blocks are separated by a space. One end of the elastic member passes through the space between the pair of blocks in the first retractor paddle. The opposite end of the elastic member passes through the space between the pair of blocks of the second retractor paddle. The hole is formed through the arcuate portion. The arcuate portion has an interior surface with a plurality of ribs extending outwardly therefrom.

The hole has a slot opening thereto. One end of the elastic member is fixed in the slot of the first retractor paddle. The opposite end of the elastic member is fixed in the slot of the second retractor paddle. The slot is tapered so as to have a wide end opening to the hole at a narrow end away from the hole.

The grasping surface comprises a plurality of fingers extending outwardly of the body portion. Each of the plurality of fingers comprises a first section connected to the body portion and extending outwardly therefrom and a second section extending transversely from an end of the first section opposite the body portion. Each of the first and second sections has an interior surface. This interior surface has a plurality of ribs extending outwardly therefrom. In the preferred embodiment of the present invention, generally semi-circular indentations are formed between adjacent pairs of the plurality of ribs. The plurality of fingers are arranged in parallel spaced relationship to each other.

In the present invention, the elastic member is a length of surgical tubing. In the preferred embodiment of the present invention, this length of surgical tubing is of a non-latex material.

DETAILED DESCRIPTION OF THE INVENTION

Figure 1:
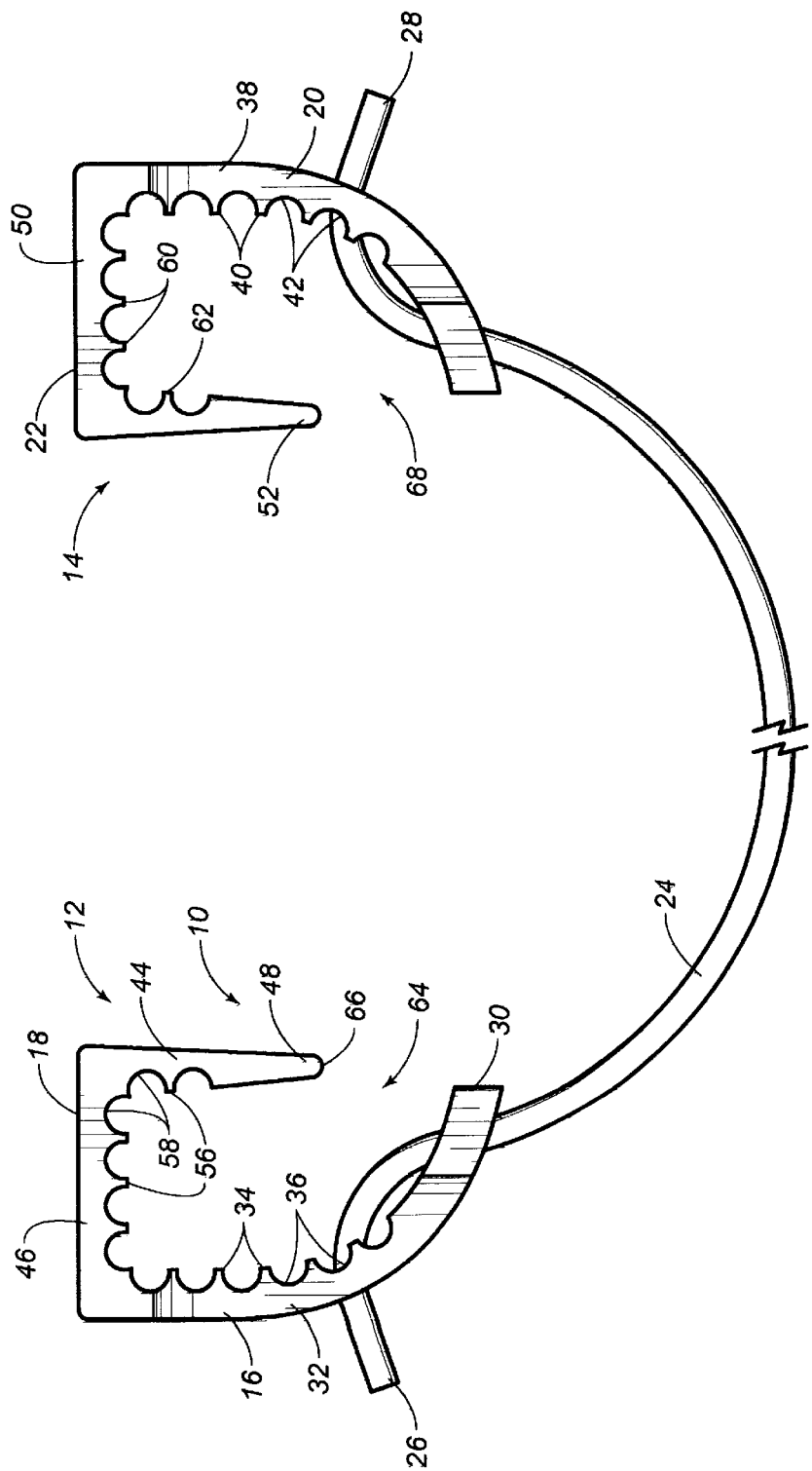
FIG. 1 is a side elevational view showing the arrangement of the circumferential retractor apparatus of the present invention.

Referring to FIG. 1, there is shown the circumferential retractor apparatus 10 in accordance with the teachings of the preferred embodiment of the present invention. The circumferential retractor apparatus 10 includes a first retractor paddle 12 and a second retractor paddle 14. The first retractor paddle 12 has a body portion 16 supporting a grasping surface 18. Similarly, the second retractor paddle 14 has a body portion 20 supporting a grasping surface 22. An elastic member 24 has one end 26 received by the first retractor paddle 12 and an opposite end 28 received by the second retractor paddle 14. As can be seen in FIG. 1, each of the retractor paddles 12 and 14 has an identical configuration.

In FIG. 1, it can be seen that the elastic member 24 is a length of surgical tubing. In use, the surgical tubing 24 will extend between a pair of blocks 30 formed at the bottom of the body portion 16 of the first retractor paddle 12. The end 26 will then pass through a hole formed in the body portion 16. The end 26 will be fixed in position by pushing downwardly on the end 26 so that the end 26 is fixed within a slot opening to the hole on the body portion 16. This arrangement is illustrated, in greater detail, in association with FIGS. 2–4. Similarly, the end 28 can be installed in the second retractor paddle 14 in the same manner that the end 26 was installed in the first retractor paddle 12.

The first retractor paddle 12 has an arcuate portion 32. The pair of blocks 30 are formed at the bottom of the arcuate portion 32. As can be seen in FIG. 1, the arcuate portion 32 has a plurality of ribs 34 extending outwardly therefrom. These ribs are formed on the interior surface of the arcuate portion 32. Semi-circular indentations 36 are formed between respective adjacent pairs of ribs 34. This configuration of ribs 34 and semi-circular indentations 36 have been found to minimize damage to the tissue received therein. The ribs 34 will serve to strongly grasp the tissue while the semi-circular indentations will distribute the force of contact over a wider area. Therefore, unlike other retractor apparatus, the present invention effectively grasps the tissue with a minimal amount of damage to such tissue.

Similarly, the second retractor paddle 14 has an arcuate section 38. Arcuate section 38 has an interior surface with a plurality of ribs 40 extending outwardly therefrom. In a similar manner to that of the first retractor paddle 12, semi-circular indentations 42 are formed between adjacent pairs of the ribs 40.

The grasping surface 18 of the first retractor paddle 12 has a plurality of fingers 44 extending outwardly of the body portion 16. Each of the plurality of fingers 44 includes a first section 46 and a second section 48. Similarly, the grasping surface 22 of the second retractor paddle 14 includes a first section 50 connected to the body portion 12 and a second section 52. The second section 22 will extend transversely downwardly from the first section 50. With respect to the first retractor paddle 12, each of the first section 46 and the second section 48 has an interior surface with a plurality of ribs 56 extending outwardly therefrom. Semi-circular indentations 58 are formed between adjacent pairs of ribs. Once again, this configuration of ribs and semi-circular indentations has been found to minimize tissue damage to the tissue received by the grasping surface. The second retractor paddle 14 also has a plurality of ribs 60 extending outwardly from the interior surface of the first section 50. The second section 52 also has ribs 62 extending outwardly from the interior surface of the second section 52.

It should be noted that the second sections 48 and 52 of the respective retractor paddles 12 and 14 extend downwardly from an end of the respective first sections 46 and 50 for a distance less than the length of the body portion 16. As such, a space 64 is formed between the end 66 of the second section 48 of the grasping surface 18 of the first retractor paddle 12 and the blocks 30. A space 68 is similarly formed with the second retractor paddle 14. Spaces 64 and 68 allow tissue sections to be introduced into the grasping surface 18.

Figure 2:
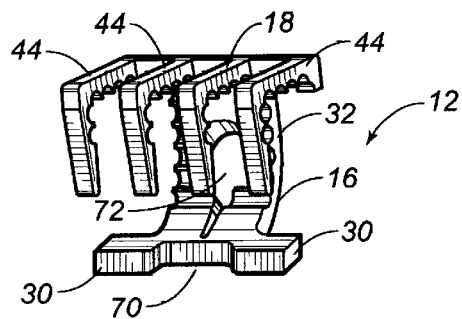
FIG. 2 is an isolated perspective view of a paddle used in the apparatus of the present invention.

FIG. 2 is an isolated view of the first retractor paddle 12. It is important to note that the second retractor paddle 14 has a similar configuration. The first retractor paddle 12 includes body portion 16 having an arcuate configuration. Blocks 30 are formed at the bottom of the arcuate portion 32. A space 70 is formed between the blocks 30 so as to allow the elastic member 24 to extend therethrough. Hole 72 is formed in the body portion 16. Specifically, the hole 72 is formed centrally of the arcuate portion 32.

In FIG. 2, it can be seen that the grasping surface 18 comprises a plurality of fingers 44. The fingers 44 are arranged in spaced parallel relationship to each other. Each of the fingers 44 includes the first section 46 and the second section 48. The distribution of the fingers 44 in spaced parallel relationship effectively grasps the tissue therein while minimizing damage to the tissue contained therein.

Figure 3:
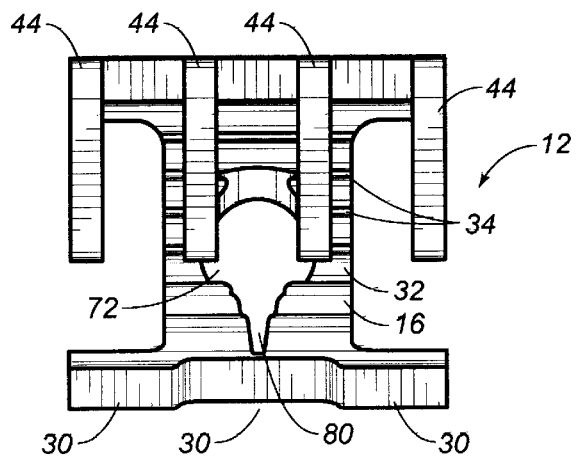
FIG. 3 is an end view showing the paddle as used in the circumferential retractor apparatus of the present invention.

FIG. 3 shows further the configuration of the hole 72 as formed in the arcuate portion 32 of body portion 16. The hole 72 is centered above the space 70 formed between the blocks 30 at the bottom of the body portion 16. The hole 72 should have a diameter somewhat larger than the diameter of the surgical tubing used for the elastic member 24. Importantly, a slot 80 opens to the hole 72 and extends downwardly toward the space 70. Slot 80 is a tapered slot which has a wide end opening to the interior of the hole 72 and a narrow end adjacent to the space 70. The slot 80 is configured so that when a downward pushing force is applied to the end 26 of the elastic member 24, the end 26 will be compressively fixed in position within the slot 80.

FIG. 3 also shows the arrangement of the fingers 44 as they extend downwardly toward the blocks 30. FIG. 3 also shows the arrangement of the ribs 34 on the interior surface of the arcuate portion 32.

Figure 4:
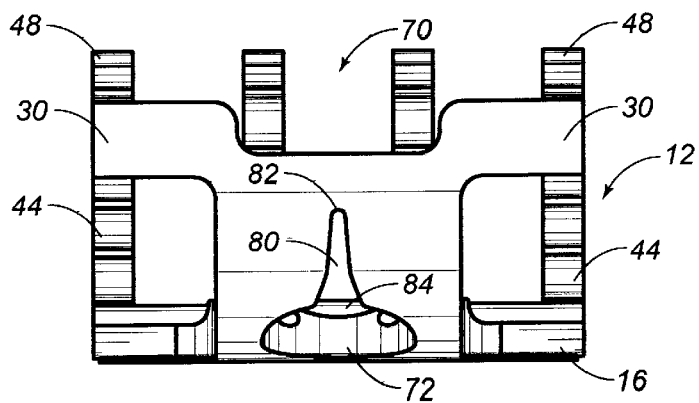
FIG. 4 is a bottom view of the paddle used in the circumferential retractor apparatus of the present invention.

FIG. 4 is a bottom view of the retractor paddle 12. In FIG. 4, it can be seen that the blocks 30 are formed at the bottom of the paddle 12. The space 70 is located between the blocks 30. The slot 80 has its narrow end 82 adjacent to the space 70. The slot 80 has its wide end 84 opening to the interior of the hole 72. In FIG. 4, it can be seen that the second section 48 of the fingers 44 extend outwardly from the body portion 16 for a greater distance than the blocks 30.

Figure 5:
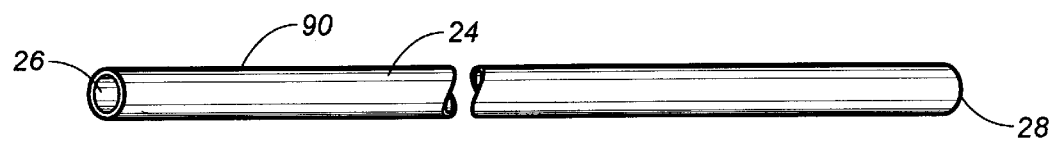
FIG. 5 is a side elevational view of the elastic member as used in the circumferential retractor apparatus of the present invention.

FIG. 5 illustrates the elastic member 24. The elastic member 24 is a length of surgical tubing 90. Surgical tubing 90 has one end 26 and another end 28. Preferably, the surgical tubing 28 is a non-latex rubber tubing. In the present invention, it is important to note that surgeons are quite familiar with the elasticity of such conventional surgical tubing. As a result, by manipulating the surgical tubing 90 during a surgical procedure, the surgeon will obtain immediate feedback as to the amount of tension that is applied to the retracted incision by the retractor paddles 12 and 14. This amount of tension can be easily adjusted by pulling on the respective ends 26 and 28 and then pushing the portions of the surgical tubing 90 adjacent to such ends downwardly into the respective slots of the paddles 12 and 14.

Figure 6:
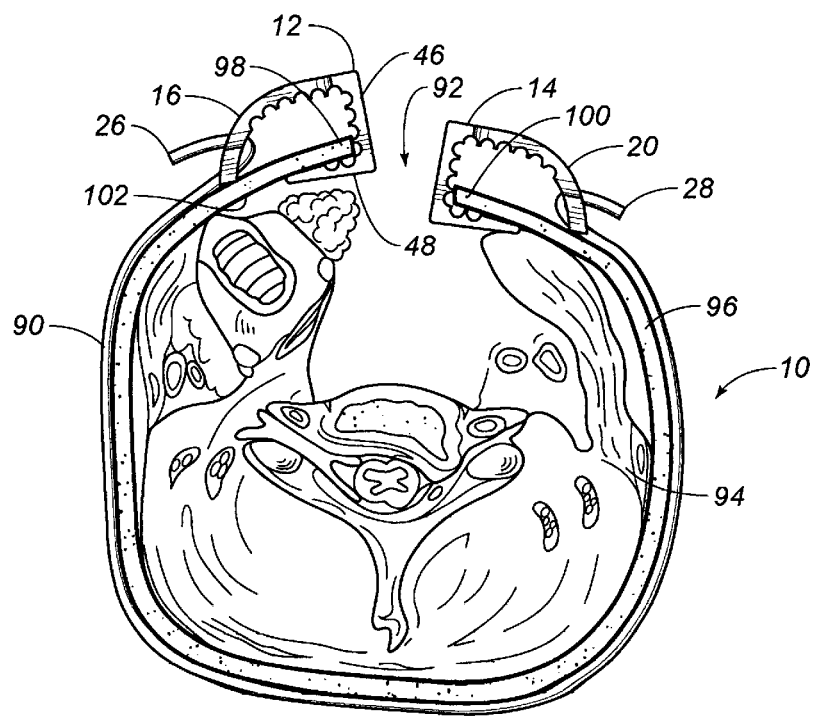
FIG. 6 is a cross-sectional view showing the application of the circumferential retractor apparatus of the present invention as applied to a surgical incision.

FIG. 6 shows the use of the circumferential retractor apparatus 10 in association with a surgical procedure. In FIG. 6, it can be seen that an incision 92 is formed in a limb 94. When this incision is made, the skin 96 will have one edge 98 and an opposite edge 100 which are separated. After an incision is made, the first retractor paddle 12 can be placed over the edge 98 such that the second section 48 will extend so as to be positioned adjacent to the interior surface 102 of the skin 96. The first section 46 of the finger 44 will extend upwardly across the edge 98 of the insized skin 96. The body portion 16 extends rearwardly of the first section 46 of the finger 44. As can be seen in FIG. 6, the surgical tubing 90 has its end 26 extending outwardly of the body portion 16. In practical application, the tubing 90 is extended through the space 70 between the blocks 30 upwardly along the interior surface of the arcuate portion 32, passed through the hole 72 and then pulled downwardly so as to fix the end 26 of the surgical tubing 90 in a proper position.

The surgical tubing 90 extends around the limb 94. It can be seen that the second retractor paddle 14 grasps the edge 100 of the skin 96 in a similar manner as did the first retractor paddle 12. The end 28 of the surgical tubing 90 is pulled through the hole formed in the body portion 20 of the second retractor paddle 14. The surgeon can then pull of the end 28 to the desired degree necessary so as to create the proper tension for pulling the edges of the skin 96 apart. The end 28 can then be locked in position by simply pulling downwardly so that the tubing 90 is compressively fixed in position in the slot associated with the body portion 20 of the second retractor paddle 14.

The surgeon can then carry out the necessary surgical procedure within the incision 92. After surgery, the surgeon can simply pull up on either of the ends 26 or 28 so as to release the surgical tubing 90 from the slots associated with the paddles 12 and 14. The surgical tubing 90 will then pull through the respective holes of the paddles 12 and 14 and be released therefrom. The retractor paddles 12 and 14 can then be simply pulled from the edges 98 and 100 of the skin 96. The incision 92 can then be closed in a conventional surgical manner.

The present invention achieves many advantages over conventional retractors. Most importantly, since the tension applied by the tubing 90 is exterior of the incision 92, and since there is no structure above the incision 92 to create an obstacle to the surgical procedure, the incision 92 will be virtually free of obstacles. The unique semi-circular indentations and ribs associated with the grasping area 18 will minimize damage to the tissue adjacent to the incision 92. Since each of the retractor paddles 12 and 14 are formed of a polycarbonate material or a LEXAN™ material, each of the retractor paddles 12 and 14 is easily sterilizable or autoclavable. Preferably, in the present invention, the surgical tubing 90 and the retractor paddles 12 and 14 are simply disposed of subsequent to the surgery.

The foregoing disclosure and description of the invention is illustrative and explanatory thereof. Various changes in the details of the illustrated construction can be made within the scope of the appended claims without departing from the true spirit of the invention. The present invention should only be limited by the following claims and their legal equivalents.

We claim:

1. A circumferential retractor apparatus comprising:

a first retractor paddle having an interior grasping surface, said first retractor paddle having a body portion supporting said grasping surface;

a second retractor paddle having an interior grasping surface, said second retractor paddle having a body portion supporting said grasping surface; and an elastic member having one end received by said first retractor paddle and an opposite end received by said second retractor paddle, said one end extending outwardly from said first retractor paddle in a direction opposite said interior grasping surface of said first retractor paddle, said opposite end extending outwardly from said second retractor paddle in a direction opposite said interior grasping surface of said second retractor paddle.

2. The apparatus of claim 1, each of said first and second retractor paddles being of an identical configuration.

3. The apparatus of claim 1, each of said first and second retractor paddles having a hole formed in said body portion, said one end of said elastic member extending through the hole in said first retractor paddle, said opposite end of said elastic member extending through the hole of said second retractor paddle.

4. The apparatus of claim 3, said body portion having an arcuate portion, said body portion having a pair of blocks connected to a bottom of said arcuate portion, said pair of blocks being separated by a space, said one end of said elastic member passing through the space of said first retractor paddle, said opposite end of said elastic member passing through the space of said second retractor paddle.

5. The apparatus of claim 4, said hole formed through said arcuate portion, said arcuate portion having an interior surface having a plurality of ribs extending outwardly therefrom.

6. The apparatus of claim 3, said hole having a slot opening thereto, said one end of said elastic member being fixed in the slot of said first retractor paddle, said opposite end of said elastic member being fixed in the slot of said second retractor paddle.

7. The apparatus of claim 6, said slot being tapered so as to have a wide end opening to said hole and a narrow end away from said hole.

8. The apparatus of claim 1, said grasping surface comprising a plurality of fingers extending outwardly of said body portion.

9. The apparatus of claim 8, each of said plurality of fingers comprising:

a first section connected to said body portion and extending outwardly therefrom; and a second section extending transversely from an end of said first section opposite said body portion.

10. The apparatus of claim 9, each of said first and second sections having an interior surface, said interior surface having a plurality of ribs extending outwardly therefrom.

11. The apparatus of claim 10, said plurality of ribs having a generally semicircular indentation formed between adjacent pairs of said plurality of ribs.

12. The apparatus of claim 8, said plurality of fingers arranged in parallel relationship to each other.

13. The apparatus of claim 1, said elastic member being a length of surgical tubing.

14. A paddle for a circumferential retractor apparatus comprising:

a paddle member having a body portion supporting a grasping surface, said body portion having a hole formed therein suitable for receiving an elastic member therein, said body portion having an arcuate portion, said body portion having a pair of blocks connected to a bottom of said arcuate portion, said pair of blocks being separated by a space, said space being suitable for allowing the elastic member to pass between said pair of blocks, said hole being formed in said arcuate portion, said arcuate portion having an interior surface with a plurality of ribs extending outwardly therefrom.

15. The paddle of claim 14, said hole having a slot opening thereto, said slot being suitable for allowing the elastic member to be fixed therein, said slot being tapered so as to have a wide end opening to said hole and a narrow end away from said hole.

16. The paddle of claim 14, said grasping surface comprising a plurality of fingers extending outwardly of said body portion.

17. The paddle of claim 16, said plurality of fingers arranged in parallel relationship to each other.

18. The paddle of claim 14, each of said plurality of fingers comprising:

a first section connected to said body portion and extending outwardly therefrom; and a second section extending transversely from an end of said first section opposite said body portion.

19. The paddle of claim 18, each of said first and second sections having an interior surface, said interior surface having a plurality of ribs extending outwardly therefrom.

* * * * *